United States Patent [19]
Binder et al.

[11] Patent Number: 4,877,809
[45] Date of Patent: Oct. 31, 1989

[54] NOVEL 2-THIENYLOXYACETIC ACID DERIVATIVES, A PROCESS FOR THEIR PREPARATION AND PHARMACEUTICAL PREPARATIONS CONTAINING THEM

[75] Inventors: Dieter Binder, Vienna; Franz Rovensky, Leitha; Hubert P. Ferber, Ansfelden, all of Austria

[73] Assignee: CL Pharma Aktiengesellschaft, Linz, Austria

[21] Appl. No.: 174,883

[22] Filed: Mar. 29, 1988

[30] Foreign Application Priority Data

Apr. 3, 1987 [AT] Austria .................................. 820/87

[51] Int. Cl.$^4$ ..................... A61K 31/38; C07D 409/00
[52] U.S. Cl. .................................. 514/444; 514/44 S; 549/59; 549/65
[58] Field of Search ..................... 549/59, 65; 514/444, 514/445

[56] References Cited

U.S. PATENT DOCUMENTS 3,832,354 8/1974 Gadient et al. .............. 260/332.2 A
4,602,016 7/1988 Cross et al. ........................ 514/234

OTHER PUBLICATIONS

Wagner Synth. Org. Chem. (1965) p. 419.
Roberts Basic Principles of Org. Chem. (1964) p. 556.

*Primary Examiner*—M. Alan Siegel
*Attorney, Agent, or Firm*—Wenderoth, Lind & Ponack

[57] ABSTRACT

The invention relates to novel 2-thienyloxyacetic acid derivatives of the general formula

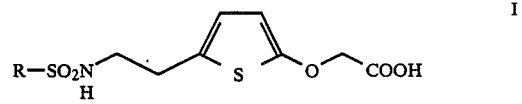

I in which R denotes a phenyl or thienyl group which is optionally mono- or polysubstituted by halogen, trifluoromethyl or $C_1$–$C_4$ alkyl, and pharmaceutically usable salts thereof, a process for the preparation of these compounds and their use for the treatment of thromboses, inflammations, high blood pressure, apoplexy and angina pectoris.

6 Claims, No Drawings

NOVEL 2-THIENYLOXYACETIC ACID DERIVATIVES, A PROCESS FOR THEIR PREPARATION AND PHARMACEUTICAL PREPARATIONS CONTAINING THEM

DESCRIPTION

The invention relates to novel 2-thienyloxyacetic acid derivatives, a process for their preparation and pharmaceutical preparations containing these substances.

Substances with an antithrombotic action have already been known for a relatively long time. Thus, for example, acetylsalicylic acid (Aspirin) also has an antithrombotic action in high doses. However, in many cases it can cause gastritis in this high dosage. Sulfated polysaccharides, such as, for example, heparins, also have an antithrombotic activity. Since these substances can cause hemorrhages, however, their use in human medicine presents problems.

It is also known that substances which inhibit thromboxane $A_2$ synthesis or block thromboxane $A_2$ receptors have an antithrombotic action. Such substances are described, for example, in U.S. Pat. Ser. No. 4,602,016, where phenoxyalkylimidazoles with an antithrombotic action are disclosed. However, since the action profile of these substances has not yet been tested and it is therefore not clear whether these substances can also really be used in human therapy, there continues to be a need for novel compounds with an antithrombotic action.

It has now been found that certain 2-thienyloxyacetic acid derivatives can block thromboxane $A_2$ receptors.

The invention thus relates to novel derivatives of 2-thienyloxyacetic acid of the general formula I

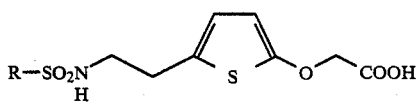

in which R denotes a phenyl or thienyl group which is optionally mono- or polysubstituted by halogen, trifluoromethyl or $C_1-C_4$ alkyl, and pharmaceutically usable salts thereof, a process for their preparation and pharmaceutical preparations containing these compounds.

Halogen is understood as being, preferably, fluorine, chlorine or bromine, in particular chlorine.

The expression "$C_1-C_4$ alkyl" used in this description designates straight-chain or branched hydrocarbon groups with 1 to 4 carbon atoms, such as methyl, ethyl, propyl, isopropyl, butyl, isobutyl and tert.-butyl.

Preferred compounds of the formula I are those in which R denotes phenyl or 4-chlorophenyl.

Particularly preferred individual compounds are: 5-(2-(benzenesulfonylamino)-ethyl)-2-thienyloxyacetic acid and 5-(2-(4-chloro-benzenesulfonylamino)-ethyl)-2-thienyloxyacetic acid.

According to the invention, the compounds of the general formula I and salts thereof are prepared by (a) oxidizing a compound of the formula II

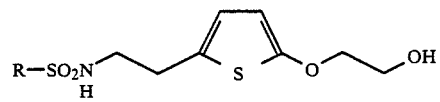

in which R has the above meaning, with silver oxide in an aqueous alkaline medium to give the acid and (b) if desired converting a free acid obtained in process step (a), of the general formula I, into a pharmaceutically tolerated salt using an inorganic or organic base.

The reaction in the process according to the invention is most advantageously carried out by dissolving the sulfonamide alcohol of the formula II in 0.5–4.0N, preferably in 2N, alkali metal hydroxide solution, adding at least 2 equivalents of $Ag_2O$ and heating the suspension at a temperature of about 75°–85° C., with stirring. The reaction time is about 2–3 hours.

The acids of the general formula I can be converted into their pharmaceutically usable salts in the customary manner using inorganic or organic bases. The salt formation can be carried out, for example, by dissolving the compounds of the formula I mentioned in a suitable solvent, for example water or a lower aliphatic alcohol, for example methanol, ethanol, propanol or isopropanol, adding an equivalent amount of the desired base, ensuring good thorough mixing and, when the salt formation has ended, distilling off the solvent in vacuo. If appropriate, the salts can be recrystallized after being isolated.

Pharmaceutically usable salts are, for example, metal salts, in particular alkali metal or alkaline earth metal salts, such as sodium, potassium, magnesium or calcium salts. Other pharmaceutically usable salts are furthermore, for example, ammonium salts which crystallize readily. The latter are derived from ammonia or organic amines, for example mono-, di- or tri-lower (alkyl, cycloalkyl or hydroxyalkyl)-amines, lower alkylenediamines or (hydroxy-lower alkyl or aryl-lower alkyl)-lower alkylammonium bases, such as, for example, methylamine, diethylamine, triethylamine, dicyclohexylamine, triethanolamine, ethylenediamine, tris(hydroxymethyl)aminomethane, benzyl trimethylammonium hydroxide and the like.

The starting compounds of the general formula II used for the process according to the invention can be prepared from known products in a manner which is known per se. In particular, they can be synthesized in accordance with the following equation and the specific information in the examples.

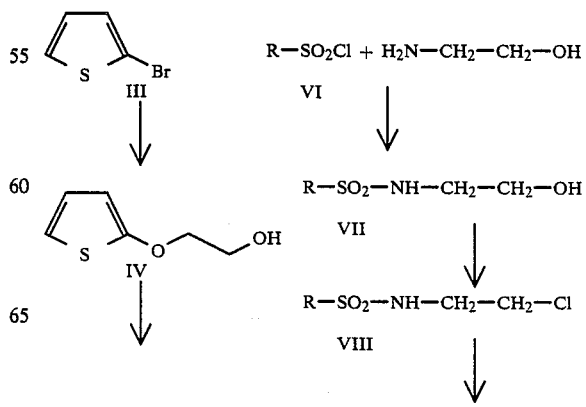

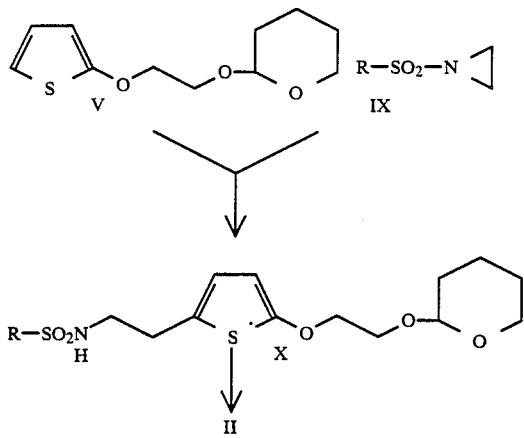

The novel compounds of the general formula I block thromboxane $A_2$ receptors in vitro and in vivo.

On the basis of these pharmacological properties, the novel compounds can be used as a medicament, by themselves or as a mixture with other active substances in the form of customary galenical formulations, on diseases caused by thromboxane $A_2$, such as, for example, thrombosis, inflammations, high blood pressure, apoplexy, asthma, shock and angina pectoris.

To determine the antithrombotic action, the substance of Example 1, 5-(2-(benzenesulfonylamino)-ethyl)-2-thienyloxyacetic acid, was compared with dazoxiben (4-(2-(1H-imidazol-1-yl)ethoxy)benzoic acid hydrochloride), an antithrombotic undergoing clinical trials, as described in Example A. This comparison showed that the antithrombotic action of the substance of Example 1 is clearly superior to the action of dazoxiben.

The compounds of the general formula I are intended for use on humans and can be administered in the customary manner, such as, for example, orally or parenterally. They are preferably administered orally, the daily dose being about 0.05 to 20 mg/kg of body weight, preferably 0.5 to 5.0 mg/kg of body weight. However, the attending doctor can also prescribe doses above or below these, depending on the general state and age of the patient, the appropriate substance of the formula I, the nature of the disease and the nature of the formulation.

If the substances according to the invention are used for prophylaxis, the doses vary approximately within the same margins as in treatment cases. Oral administration is also preferred for prophylaxis.

The compounds of the formula I can be administered by themselves or in combination with other pharmaceutically active substances, the content of compounds of the formula I being between 0.1 and 99%. The pharmaceutically active compounds are in general present in a mixture with suitable inert auxiliaries, excipients and/or diluents, such as, for example, pharmaceutically acceptable solvents, gelatine, gum arabic, lactose, starch, magnesium stearate, talc, vegetable oils, polyalkylene glycol, petroleum jelly and the like.

The pharmaceutical preparations can be in solid form, for example as tablets, coated tablets, suppositories, capsules and the like, in semi-solid form, for example as ointments, or in liquid form, for example as solutions, suspensions or emulsions. If appropriate, they are sterilized and contain auxiliaries, such as preservatives, stabilizers, emulsifying agents, salts for modifying the osmotic pressure and the like. In particular, pharmaceutical preparations can contain the compounds according to the invention in combination with other therapeutically useful substances. The compounds according to the invention can be formulated with these, for example, together with the abovementioned auxiliaries, excipients and/or diluents to give combination preparations.

EXAMPLE 1

5-(2-(Benzenesulfonylamino)-ethyl)-2-thienyloxyacetic acid 19.3 g (0.1136 mol) of silver nitrate are dissolved in 120 ml of distilled water, and a solution of 4.5 g (0.1136 mol) of sodium hydroxide in 50 ml of distilled water is slowly added dropwise, with stirring. The resulting suspension of silver oxide is stirred for a further 10 minutes and the precipitate is filtered off and washed several times with distilled water.

9.3 g (0.029 mol) of N-(2-(2-(5-(2-hydroxy)-ethoxy)-thienyl)-ethyl)-benzenesulfonamide are dissolved in 90 ml of 2N aqueous sodium hydroxide solution, the still moist silver oxide is added and the mixture is heated to 80° C., with mechanical stirring. After 3 hours at this temperature, the suspension is cooled and filtered over HYFLO. The clear solution in sodium hydroxide solution is acidified with about 6 ml of concentrated hydrochloric acid and extracted three times with 100 ml of ether each time.

The ethereal phase is extracted three times by shaking with 100 ml of saturated sodium bicarbonate solution each time, and the extract is washed once with 50 ml of ether and acidified with concentrated hydrochloric acid. The aqueous phase is extracted twice with 150 ml of ether and the combined ether phases are dried over sodium sulfate, filtered and evaporated. The crystalline residue is digested with 30 ml of diisopropyl ether and filtered off.

Yield: 2.6 g of colorless crystals (26.4% of theory)
Melting point: 110°–113° C. (ether/diisopropyl ether)
$^1$H-NMR: (DMSO) delta (ppm): 9.16 (s; broad; 1H; —COOH), 7.67–7.88 (h; 2H; B—$H_2$, B—$H_6$), 7.47–7.55 (h; 3H; B—$H_3$, B—$H_4$, B—$H_5$), 7.27; 7.33; 7.47 (t; 1H; —NH—) 6.02; 6.06; 6.33; 6.38 (AB; 2H; Th—$H_3$; Th—$H_4$; $J_{34}$=3.7 Hz), 4.51 (s; 2H; O—$CH_2$—CO), 2.57–2.99 (h; 4H; —$CH_2$—$CH_2$—)
$^{13}$C-NMR: (DMOS) delta (ppm): 169.10 (s; —COOH), 161.95 (s; Th—$C_2$), 140.27 (s; B—$C_1$), 131.77 (s; B—$C_4$), 128.52 (d; B—$C_3$, B—$C_5$), 127.7 (s; Th—$C_5$), 126.29 (d; B—$C_2$, B—$C_6$), 121.96 (d; Th—$C_4$), 105.27 (d; Th—$C_3$), 69.46 (t; O—$CH_2$—CO), 43.77 (t; —NH—$CH_2$—), 30.18 (t; TH—$CH_2$—).

The starting material can be prepared as follows:

2-(2-Thienyloxy)-ethanol (IV)

323.7 ml of 5.4M sodium methylate solution (1.75 mol) are added to 1,600 ml of absolute ethylene glycol. The reaction mixture is heated and the methanol formed is distilled off over a reflux divider, while passing through nitrogen, until the bottom temperature rises to 130° C. When the removal of methanol has ended, 187.5 g (1.15 mol) of 2-bromothiophene, 55.5 g of finely ground copper oxide and 5.6 g of sodium iodide are added, the apparatus is further flushed briefly with nitrogen and closed with a flask and the mixture is stirred at 80° C. for 175 hours.

The reaction mixture is then cooled and filtered with suction over HYFLO. The filtrate is diluted with 800 ml of water and acidified slightly with concentrated hydrochloric acid.

The mixture is extracted four times with 400 ml of methylene chloride each time (1,600 ml in total). The combined organic phases are extracted once by shaking with 200 ml of water, dried over sodium sulfate, filtered and evaporated. The residue is distilled.

Yield: 102.7 g of a colorless oil (62% of theory)
Boiling point: 90°–95° C./0.6 mbar N-(2-(2-(5-(2-Hydroxy)-ethoxy)-thienyl)-ethyl)-benzenesulfonamide 30 g (0.208 mol) of 2-(2-thienyloxy)-ethanol are taken in 300 ml of absolute tetrahydrofuran, and 10 mg of p-toluenesulfonic acid are dissolved therein. 18.37 g (0.212 mol) of 3,4-dihydropyran are added to the solution and the mixture is stirred for 8 hours.

The mixture is cooled to $-20°$ C. and 12.6 ml (0.028 mol) of a 2.5M solution of n-butyllithium in n-hexane are added dropwise, with stirring, such that the temperature does not rise above $-10°$ C. The mixture is allowed to warm to room temperature and is stirred for one hour.

The reaction mixture is cooled to 10° C. and a solution of 19.05 g (0.104 mol) of N-benzenesulfonylaziridine (DRP 698,597 (1939)) in 100 ml of absolute tetrahydrofuran is added dropwise at 10°–15° C. in the course of 30 minutes. The mixture is heated to room temperature and stirred for a further 2 hours.

The mixture is emptied onto 200 ml of 2N aqueous HCl and extracted three times with 120 ml of methylene chloride each time. The combined organic phases are dried over sodium sulfate, filtered and evaporated. The residue is taken up in 300 ml of absolute methanol, 2 ml of 30% strength methanolic hydrochloric acid are added and the mixture is stirred at room temperature for 10 minutes. After addition of 2 g of sodium carbonate, the mixture is evaporated in vacuo.

The residue is partitioned between 250 ml of 1N aqueous sodium hydroxide solution and 200 ml of ether and the ethereal phase is rinsed once with 50 ml of 1N sodium hydroxide solution. The combined aqueous phases are washed twice with 100 ml of ether each time, acidified with about 25 ml of concentrated hydrochloric acid and extracted three times with 150 ml of methylene chloride each time. The methylene chloride phase is dried over sodium sulfate, 3 g of active charcoal are added, and the mixture is filtered and evaporated.

Yield: 33.3 g of a dark red oil (97.8% of theory), which is used directly in the next stage.

EXAMPLE 2

5-(2-(4-Chloro-benzenesulfonylamino)-ethyl)-2-thienyloxyacetic acid 15 g (0.088 mol) of silver nitrate were dissolved in 90 ml of distilled water, and a solution of 3.5 g (0.088 mol) of sodium hydroxide in 45 ml of distilled water were slowly added dropwise, with stirring. The resulting suspension of silver oxide was stirred for a further 10 minutes and the precipitate was filtered off and washed several times with distilled water.

4.0 g (0.011 mol) of 4-chloro-N-(2-(2-(5-(2-hydroxy)-ethoxy)-thienyl)ethyl)-benzenesulfonamide (II) were dissolved in 40 ml of 2N aqueous sodium hydroxide solution, the still moist silver oxide was added and the mixture was heated to 80° C., with mechanical stirring.

After 3.5 hours at this temperature, the suspension was cooled and filtered with suction over HYFLO and the residue was rinsed with 2N aqueous sodium hydroxide solution. The clear solution in sodium hydroxide solution was acidified with concentrated hydrochloric acid and extracted three times with 80 ml of ether each time.

The ethereal phase was extracted twice by shaking with 50 ml of saturated sodium bicarbonate solution each time, washed once with 50 ml of ether and acidified with concentrated hydrochloric acid. The aqueous phase was extracted twice with 150 ml of ether and the combined ether phases were dried with sodium sulfate, filtered and evaporated. The crude product was recrystallized from toluene.

Yield: 1.3 g of colorless crystals (31.7% of theory)
Melting point: 125°–127° C. (toluene)
Thin layer chromatography: benzene:dioxane:glacial acetic acid=8:1:1; Rf about 0.3

$^1$H-NMR: (CDCl$_3$) delta (ppm): 7.81; 7.71; 7.51; 7.42 (AB; 4H; Bz—C$_3$, Bz—C$_5$; Bz—C$_2$, Bz—C$_6$; $J_{AB}$=8.0 Hz), 6.39; 6.35; 6.10; 6.06 (AB; 2H; ThH$_3$; ThH$_4$; $J_{AB}$=3.8 Hz), 4.85 (t; 1H; —NH—), 4.61 (s; 2H; —O—CH$_2$—COO—), 3.13 (t; 2H; N—CH$_2$—; J=6 Hz), 2.80 (t; 2H; Th—CH$_2$—; J=6 Hz)

$^{13}$C-NMR: (DMSO) delta (ppm): 169.0 (s; —COOH), 161.9 (s; Th—C$_2$), 139.3 (s; Bz—C$_1$), 137.1 (s; Bz—C$_4$), 129.1 (d; Bz—C$_3$, B—C$_5$), 128.2 (d; Bz—C$_2$, Bz—C$_6$), 127.4 (Th—C$_5$), 122.4 (d; Th—C$_4$), 105.1 (d; Th—C$_3$), 69.4 (t; O—CH$_2$—CO), 43.8 (t; —NH—CH$_2$—), 29.9 (t; Th—CH$_2$)

The starting material can be prepared as follows:

4-Chloro-(2-(2-(5-(2-hydroxy)-ethoxy)-thienyl)-ethyl)-benzenesulfonamide (II)

18.9 g (0.137 mol) of 2-(2-thienyloxy)-ethanol were taken in 200 ml of absolute tetrahydrofuran, and about 50 mg of p-toluenesulfonic acid were dissolved therein. 14.2 g (0.169 mol) of 3,4-dihydropyran were added and the mixture was stirred for 8 hours.

The mixture was cooled to $-20°$ C. and 66 ml (0.165 mol) of a 2.5M solution of n-butyllithium in n-hexane were added dropwise, with stirring, such that the temperature did not rise above $-15°$ C. The mixture was allowed to warm slowly to room temperature and stirring was continued for one hour.

A solution of 18 g (0.083 mol) of N-(4-chlorobenzenesulfonyl)-aziridine (V. I. Markov and D. A. Danileiko, Zh. Org. Khim 1973 (6), 1357) in 100 ml of absolute tetrahydrofuran was now added dropwise at $-5°$ to 0° C. The reaction mixture was heated to room temperature and stirred for a further 30 minutes.

The reaction mixture was emptied onto 200 ml of 2N aqueous HCl and extracted three times with 250 ml of methylene chloride each time. The combined organic phases were dried with sodium sulfate, filtered and evaporated. The residue was taken up in 100 ml of absolute methanol, 10 ml of 30% strength methanolic hydrochloric acid were added, and the mixture was stirred at room temperature for 10 minutes. A spoonful of sodium carbonate was added and the methanol was distilled off. The residue was partitioned between 100 ml of 1N aqueous sodium hydroxide solution and 100 ml of ether and the ethereal phase was rinsed once with 100 ml of 1N sodium hydroxide solution. The combined aqueous phases were washed twice with 50 ml of ether, acidified with concentrated hydrochloric acid and extracted three times with 100 ml of methylene chloride each time. Thereafter, the extract was dried over sodium sulfate, active charcoal was added, the mixture was filtered and the filtrate was evaporated. 10.15 g of a viscous dark oil were obtained. This highly contaminated crude product was filtered over silica gel 60 (180 g of silica gel, eluting agent: ethyl acetate:petroleum ether).

Yield: 4.5 g of colorless crystals (15% of theory)
Melting point: 85°–87° C. (benzene)

EXAMPLE A

Investigation of the antithrombotic activity

Male Wistar rats (SPF) weighing 200–300 g were anesthetized with pentobarbital sodium (60 mg/kg intraperitoneally). The animals were then given an intravenous injection of the substance of Example 1 ("Substance A") or dazoxiben (4-(4-(1H-imidazol-1-yl)ethoxy)benzoic acid hydrochloride) ("Substance B"). A venule of the mesenterium was exposed, clipped to the stage of a microscope and flushed with a constant 2.5 ml/minute of physiological saline solution. Half an hour after injection of the test substance, a laser beam from a Coherent CR 2 supergraphite ion laser (argon laser) was directed onto the venule through the 50× interference contrast objective of a Leitz Orthoplan microscope for a duration of 1/30 second. The initial energy under the objective of the microscope was 0.18 watt. If no platelet thrombus formed after the first laser lesion (=laser shot) or if the thrombus did not correspond to the vessel diameter in length and width, further laser shots were fired to produce a thrombus which corresponded to the vessel diameter in length and width.

The number of laser shots here is a measure of the antithrombotic activity of the test substances: the higher the number of laser shots for the same vessel diameter, the greater the antithrombotic effect.

Animals which had received no test substances were used as controls.

The tests were carried out on 5 animals per test substance and concentration, 3 vessels with a diameter of between 20 and 30 μm being damaged per animal. Statistical evaluation was by the Kruskal and Wallis test and by the Dunn rank sum test.

RESULTS

The results of the experiments are summarized in Table 1:

| Concentration (mg/kg) | Number of laser shots (mean value) | |
|---|---|---|
| | Substance A | Substance B |
| 0 (control) | 2,93 ± 0,36 | 2,93 ± 0,36 |
| 1 | 3,12 ± 0,52 | 3,07 ± 0,47 |
| 5 | 6,40 ± 0,56 | 2,89 ± 0,57 |
| 10 | 6,13 ± 0,30 | 3,14 ± 0,66 |
| 15 | 6,33 ± 0,53 | 4,46 ± 0,48 |
| 20 | 6,42 ± 0,41 | 6,35 ± 0,55 |

DISCUSSION

The start of the antithrombotic action is 1 mg/kg of body weight for substance A and reaches a maximum at 5 mg/kg. A further increase in concentration provides no further increase in action. In order to achieve an action comparable to the action maximum of substance A using substance B, injection of 20 mg/kg, that is to say 4 times the amount, is necessary.

We claim:

1. A compound of the formula I

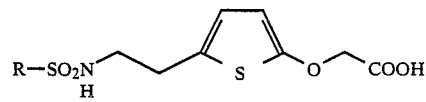

in which R denotes a phenyl or thienyl group which is optionally mono- or polysubstituted by halogen, trifluoromethyl or $C_1$–$C_4$ alkyl, or a pharmaceutically usable salt thereof.

2. A compound of formula I as claimed in claim 1, in which R denotes phenyl.

3. A compound of formula I also claimed in claim 1, in which R denotes 4-chlorophenyl.

4. The compound 5-(2-benzenesulfonylamino)-ethyl)-2-thienyloxyacetic acid, as claimed in claim 1.

5. The compound 5-(2-(4-chloro-benzenesulfonylamino))-ethyl)-2-thienyloxyacetic acid, as claimed in claim 1.

6. A pharmaceutical composition for the treatment of thrombosis in man which comprises an anti-thrombotic effective amount of a compound as claimed in claim 1 or a pharmaceutically acceptable salt thereof and a pharmaceutically acceptable excipient, carrier or diluent therefor.

* * * * *